United States Patent [19]

Chriswell

[11] Patent Number: 5,181,428
[45] Date of Patent: Jan. 26, 1993

[54] METHOD AND MEANS FOR TESTING SOIL SAMPLES

[75] Inventor: Colin D. Chriswell, Slater, Iowa

[73] Assignee: Iowa State University Research Foundation, Inc., Ames, Iowa

[21] Appl. No.: 530,903

[22] Filed: May 29, 1990

[51] Int. Cl.$^5$ .............................................. G01N 33/24
[52] U.S. Cl. .................................. 73/863.12; 73/866;
436/178; 436/31; 436/139
[58] Field of Search ................ 73/863.12, 866, 863.23,
73/863.25, 863, 864.91; 422/68.1, 69; 436/178,
36, 31, 60, 139

[56] References Cited

U.S. PATENT DOCUMENTS

| 2,095,056 | 10/1937 | Clough | 436/178 X |
| 2,733,135 | 1/1956 | Huckabay | 436/31 |
| 3,020,975 | 2/1962 | Lupfer | 73/863.12 X |
| 3,926,718 | 12/1975 | Guilbault et al. | 162/164.6 X |
| 4,759,227 | 7/1988 | Timmon | 73/863.23 |
| 4,990,773 | 2/1991 | Supernaw et al. | 436/31 X |

FOREIGN PATENT DOCUMENTS

| 1050573 | 2/1959 | Fed. Rep. of Germany | 73/866 |
| 2909872 | 9/1980 | Fed. Rep. of Germany | 436/178 |
| 996618 | 2/1983 | U.S.S.R. | 73/866 |
| 1449907 | 1/1989 | U.S.S.R. | 73/866 |

OTHER PUBLICATIONS

"Rapid and Convenient Laboratory Method for Extraction and Subsequent Spectrophotometric Determination of Bitumen Content of Bituminous Sands"; *Analytical Chemistry*, vol. 46, No. 6, May 1974, pp. 794–795; by M. Patel.

*Primary Examiner*—Tom Noland
*Attorney, Agent, or Firm*—Zarley, McKee, Thomte, Voorhees & Sease

[57] ABSTRACT

A device for testing soil samples is comprised of a closed container having an interior compartment with upper and lower portions. A valve is provided for introducing into the closed container a liquid having the general properties of butane, and a second valve is provided in the container for allowing gas in the closed container to exit therefrom. A soil sample filter container is suspended within the container above the bottom portion thereof. A condensation element is mounted in the closed container and positioned above the filter container to cause gas evaporating from the liquid in the container to liquefy as condensate on the condensation element, whereupon the condensate drips into the filter container and leaches through a soil sample therein, and then collects as a liquid in the bottom portion of the closed container. This permits a hydrocarbon residue to be left in the bottom portion of the container after the outlet valve has been opened to permit the liquid to evaporate.

10 Claims, 1 Drawing Sheet

METHOD AND MEANS FOR TESTING SOIL SAMPLES

BACKGROUND INVENTION

Many states have now passed laws requiring the periodic monitoring of all underground storage tanks to assure that leakages are not a source of ground water contamination. Federal agencies are also requiring similar regulations. This monitoring is best performed in the field using portable instrumentation. Sample wells are drilled in the vicinity of underground storage tanks, and ground water from the sampling wells is analyzed to determine if contaminates arising from leaking storage tanks is present. In cases where the sampling wells are dry, soil samples are analyzed to determine if contaminates are present.

Procedures are available for the field sampling, extraction and analysis of water samples taken from sampling wells. However, efficient procedures are not available for the extraction of soil samples in the field.

The current and proposed regulations requiring monitoring of underground storage tanks have created a need for a simple, rapid, sensitive, field-usable device for determining hydrocarbons in soil samples. Portable gas chromatographs are available for determining hydrocarbons once the hydrocarbons are isolated from a soil sample. However, no satisfactory field-usable means exist for isolating hydrocarbons from solid samples. Headspace and purge and trap procedures are effective in laboratory environments for the isolation of gasoline from soil samples, but they are not usable in field situations by non-technically trained personnel. Solvent extraction procedures are also effective in laboratory situations for isolating gasoline, diesel fuel, fuel, oil and other hydrocarbons from soil samples, but they are far too complex for field use. In addition, the presently available sampling procedures do not provide the required detection limits unless very large soil samples are taken. This may pose a problem when samples are isolated from narrow bore monitoring wells.

It is therefore the principal object of this invention to provide a method and means for testing soil samples that can quickly and easily be conducted in the field by non-technical persons.

It is a further object of this invention to provide a method and means for testing soil samples which will yield a sample of hydrocarbons from a small soil sample for subsequent gas chromatographic analysis.

A further object of this invention is to provide a method and means for testing soil samples that will be completely portable and which will require no supporting utilities. (Conventional procedures do require cooling water, electricity, and pressurized gases.)

A further object of this invention is to provide a method and means for testing soil samples that is economical.

These and other objects will be apparent to those skilled in the art.

SUMMARY OF THE INVENTION

A method for testing soil samples comprising the taking of a small soil sample and depositing the same within a filter container capable of retaining the soil sample and also capable of passing liquid material. The filter container is suspended in a closed container having bottom and top portions at a position above the bottom portion thereof. The closed container is then charged with a quantity of butane liquid.

A condensation element is suspended over the filter container to cause butane liquid to condense thereon from the butane gas evaporating from the butane liquid introduced into the closed container. The condensed butane liquid then drips by gravity into the filter container to leach through the soil sample, and thence to pass through the filter container to accumulate in the bottom portion of the closed container.

The closed container is then opened after a period of time to permit the liquid butane to evaporate, and to leave behind in the bottom of the closed container a sample of hydrocarbon residue resulting from said liquid butane having leached through the soil sample. The hydrocarbon residue is then analyzed to determine the concentration and identity thereof.

The device for testing soil samples is comprised of a closed container having an interior compartment with upper and lower portions. A means is provided for introducing into said closed container a liquid having the general properties of butane, and a closable means is provided in the container for allowing gas in the closed container to exit therefrom.

A soil sample filter container is suspended within the container above the bottom portion thereof. A condensation means is mounted in the closed container and positioned above the filter container to cause gas evaporating from the liquid in the container to liquefy as condensate on the condensation means, whereupon the condensate drips into the filter container and leaches through a soil sample therein, and then collects as a liquid in the bottom portion of the closed container. This permits a hydrocarbon residue to be left in the bottom portion of the container after the closable means has been opened to permit the liquid to evaporate.

DESCRIPTION OF THE PREFERRED EMBODIMENT

Figures 1, 2:
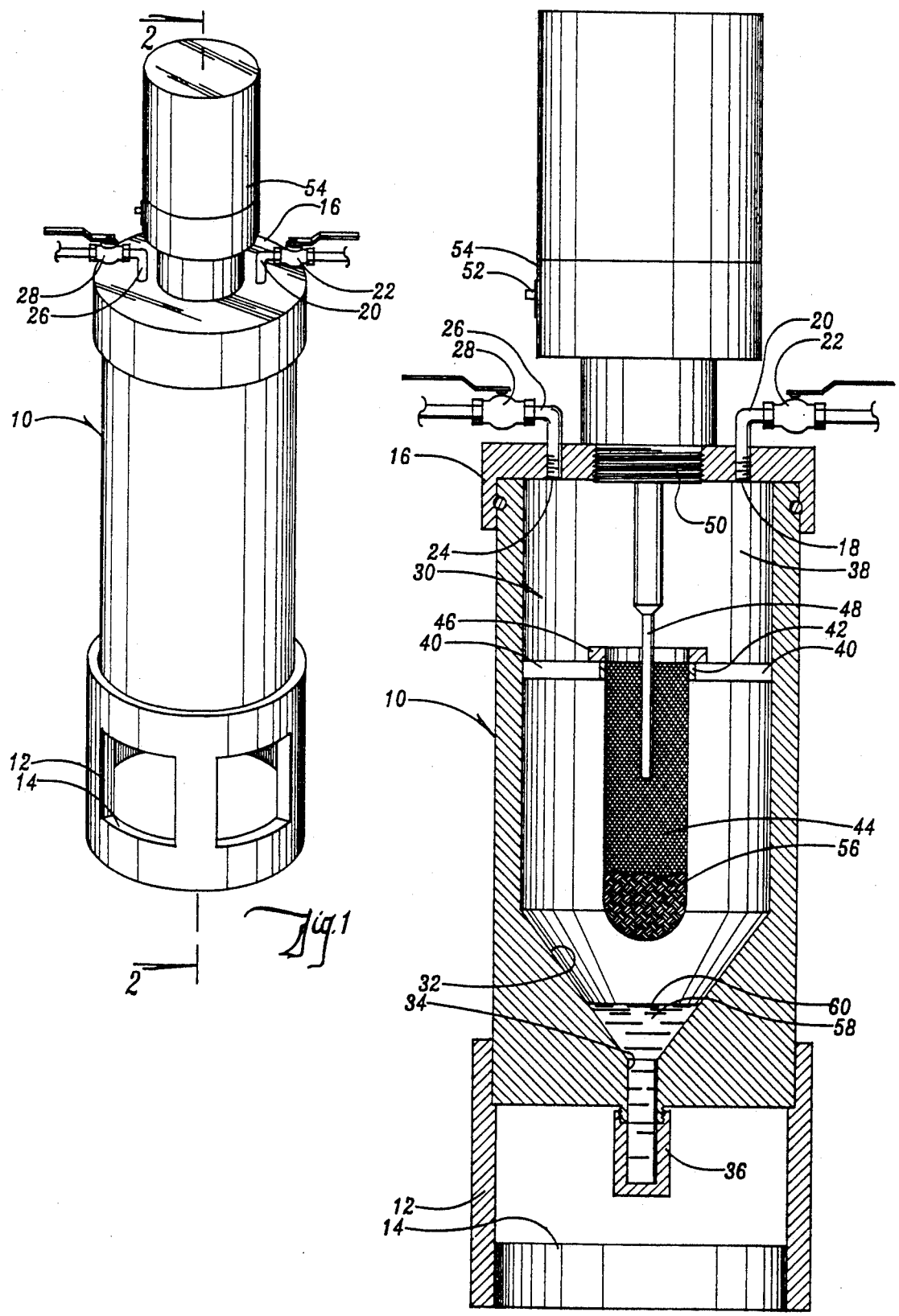
FIG. 1 is a perspective view of the device of this invention.
FIG. 2 is a sectional view taken on line 2—2 of FIG. 1.

The number 10 designates a closed container 10 comprised of plastic or the like. Container 10 has a plurality of legs 12 which are secured to a supporting base 14.

A lid 16 is in sealed condition on the top of container 10. Lid 16 has an inlet port 18 to which is connected inlet line 20 with valve 22 imposed therein. Components 18, 20 and 22 are adapted to charge the container with a quantity of liquid butane, as will be discussed hereafter.

Numeral 24 designates a gas relief port to which is connected relief line 26. Valve 28 is imposed in line 26 which in turn empties into the atmosphere.

Compartment 30 within closed container 10 has a tapered lower portion 32 which terminates in well 34. A thimble 36 is threaded into the bottom of container 10 and extends therebelow so that it can be selectively removed therefrom at the completion of the method, as will be discussed hereafter.

Compartment 30 has an upper portion 38. Radial arms 40 extend inwardly from the outer walls of compartment 30 and terminate in a central ring 42. A filter container 44 has an upper flange 46. Filter container 44 is suspended below ring 42 by means of the upper flange 46 resting on the top of the ring 42.

A condensation means 48 extends downwardly into compartment 30 and into the filter container 44 from threaded plug 50 which is threadably mounted in a suitable threaded aperture in lid 16. Means 48 is comprised of conventional battery operated Peltier junction cooling elements which is controlled by switch 52 on conventional battery 54.

Filter container 44 can assume a variety of designs. A conventional Soxhlet thimble is suitable for use.

In operation, threaded plug 50 is removed from lid 16 along with battery 54 and condensation means 48 which are secured thereto. A soil sample 56 is then deposited in filter container 4, and the screw plug 50 is then replaced. This closes and seals the compartment 30.

A quantity of liquid butane is introduced into compartment 30 through port 18 by opening valve 22. The source of liquid butane (not shown) is at the convenience of the operator. The liquid butane 58 is filled to the approximate level indicated by the numeral 60 in FIG. 2. At ambient temperatures, the liquid butane inside the compartment will create pressure of about 30 psi as the butane begins to evaporate within the container from the upper level 60 thereof. In order to make sure that all of the air has been expelled, the valve 28 may be intermittently opened to allow the air to escape.

The switch 52 is actuated to cause the condensation means 38 to function, and it is left on for a period of 30 minutes. More than 30 minutes will be required if heavier hydrocarbons, such as diesel fuel, were being extracted or if a particularly non-porous soil were being extracted.

During this period of time, butane vapors will condense on the condensation means 48, which should be maintained at a temperature of about $-10°$ C. The liquidified butane condensing on means 48 will drip through the soil sample extracting any hydrocarbons, and will then pass through the filter container 48 into the lower portion 32 of the chamber 30. The compartment 30 will be at a ambient temperature about 20° C. As butane liquid condenses on the condensation means 48, fresh butane will evaporate from the surface 60 of the liquid 58 to maintain a pressure of approximately 30 psi. Thus, the soil sample 56 will continuously be extracted with freshly distilled butane liquid. Because hydrocarbons of interest have a negligible partial pressure at the operating temperature of the device, they will remain in the bottom of the compartment 30. At the conclusion of the extraction interval, the pressure will be released from the extractor by opening valve 28. The volatile n-butane, which has a boiling point of $-0.5°$ C., will evaporate through port 24 in line 26. The extracted hydrocarbons will accumulate in the bottom of thimble 36.

When all of the liquid butane 58 has been evaporated through the line 26, thimble 36 is unthreaded and the hydrocarbon residue therein can be evaluated by gas chromatographic analysis. When the butane has evaporated the top of the extractor is removed. If a significant amount of hydrocarbon residue is present, a sample is withdrawn directly for gas chromatographic analysis using a microliter syringe. If, however, there is too little material in the tip to sample, a measured amount of an appropriate solvent is added to the tip to dissolve the sample. An aliquot of the sample dissolved in the solvent is then withdrawn for analysis.

It should be understood that the basic procedure described herein is very similar to classical Soxhlet extraction procedures for the isolation of components from samples. However, the use of liquidified butane as the solvent, and the structure of the device in which the extraction is performed, are believed to be unique.

From the foregoing, it is seen that this invention will achieve at least its stated objectives.

I claim:

1. A device for testing soil samples to determine the presence of hydrocarbon contaminants, comprising, a closing container having an interior compartment having upper and lower portions, means for introducing into said container a liquid having the general properties of butane, said general properties including being a hydrocarbon, being in a gaseous state under normal temperature and pressure, and being convertible to a liquid state when subjected to pressure, operator closable means for maintaining sufficient pressure within said closed container to liquefy at least a portion of the liquid and for allowing pressure in the closed container to e released to allow at least a portion of the liquid to return to a gaseous state and to exit from said container, a soil sample filter container suspended in said container above said bottom portion thereof, and a condensation means in said closed container and positioned above said filter container to cause gas evaporating from said liquid to liquefy as condensate on said condensation means, to drip into said filter container and to leach through a soil sample therein, and to collect in the bottom portion of said closed container, whereby a hydrocarbon residue will be left int eh bottom portion of said container after said closeable means has been opened to permit said liquid to evaporate.

2. The device of claim 1 wherein a quantity of liquid butane is located in the bottom of closed container.

3. The device of claim 1 wherein said filter container is a Soxhlet thimble.

4. The device of claim 1 wherein said condensation means extends into said filter container.

5. The device of claim 1 wherein said condensation means is secured to a threaded plug in a cover for said closed container.

6. The device of claim 5 when a battery is operatively secured to the outside of said container and is electrically connected to said condensation means.

7. A device for testing soil samples to determine the presence of hydrocarbon contaminants, comprising, a closed container having an interior compartment having upper and lower portions, means for introducing into said container a liquid having the general properties of butane, means for locating a quantity of butane in the bottom of the lower portions of the interior compartment of said closed container, closable means for allowing gas in said closed container to exit from said container, a soil sample filter container suspended in said container above the bottom portion thereof, and a condensation means in said closed container and positioned above said filter container to cause gas evaporating from said liquid to liquefy as condensate on said condensation means, to drip into said filter container and to leach through a soil sample therein, and to collect in the bottom portion of said closed cntainer, whereby a hydrocarbon residue will be left in the bottom portion of said container after said closable means has been opened to permit said liquid to evaporate.

8. The device of claim 7 wherein said condensation means extends into said filter container.

9. The device of claim 7 wherein said condensation means is secured to a threaded plug in a cover for said closed container.

10. The device of claim 9 wherein a battery is operatively secured to the outside of said container and is electrically connected to said condensation means.

* * * * *